(12) United States Patent
Tsao et al.

(10) Patent No.: US 9,599,700 B2
(45) Date of Patent: Mar. 21, 2017

(54) ULTRASOUND DIAGNOSIS APPARATUS

(75) Inventors: Jing-Wen Tsao, Tokyo (JP); Masanori Hisatsu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 791 days.

(21) Appl. No.: 12/626,215

(22) Filed: Nov. 25, 2009

(65) Prior Publication Data

US 2010/0145198 A1 Jun. 10, 2010

(30) Foreign Application Priority Data

Dec. 4, 2008 (JP) .................................. 2008-310023

(51) Int. Cl.
*A61B 8/00* (2006.01)
*G01S 7/52* (2006.01)
*G01S 15/89* (2006.01)

(52) U.S. Cl.
CPC ............ *G01S 7/52047* (2013.01); *A61B 8/54* (2013.01); *A61B 8/00* (2013.01); *G01S 15/8918* (2013.01)

(58) Field of Classification Search
USPC ............ 600/407, 437–461; 73/601, 625, 626
See application file for complete search history.

(56) References Cited

U.S. PATENT DOCUMENTS

| 4,691,570 A | 9/1987 | Hassler |
| 5,685,308 A | 11/1997 | Wright et al. |
| 5,817,023 A * | 10/1998 | Daft .............................. 600/447 |
| 6,056,693 A * | 5/2000 | Haider .......................... 600/443 |
| 6,056,694 A * | 5/2000 | Watanabe et al. ............. 600/447 |
| 6,289,231 B1 | 9/2001 | Watanabe et al. |
| 6,629,929 B1 | 10/2003 | Jago et al. |
| 2005/0203412 A1 | 9/2005 | Amemiya |
| 2009/0069693 A1* | 3/2009 | Burcher .............. G01S 7/52028 600/459 |

FOREIGN PATENT DOCUMENTS

| JP | 07-116163 A | 5/1995 |
| JP | 10-258052 A | 9/1998 |
| JP | 2002-515115 A | 5/2002 |

(Continued)

OTHER PUBLICATIONS

European Search Report dated Apr. 16, 2010, issued in corresponding European Patent Application No. 09014375.1.

(Continued)

*Primary Examiner* — Amanda Lauritzen Moher
*Assistant Examiner* — Shahdeep Mohammed
(74) *Attorney, Agent, or Firm* — Westerman, Hattori, Daniels & Adrian, LLP

(57) ABSTRACT

In FIG. 2 (A), a reception beam (102) is formed using a weighting function (112). A position of a peak of the weighting function (112) is set at the position of the reception beam (102). A reception beam (104) is formed using a weighting function (114), and a position of a peak of the weighting function (114) is set at the position of the reception beam (104). A reception beam (106) is formed using a weighting function (116) and a position of a peak of the weighting function (116) is set at a position of the reception beam (106). In this manner, the positions of the peaks of the weighting functions (112, 114, 116) are shifted in the receive aperture, to follow movements of the reception beams (102, 104, 106) caused by electrical scanning.

14 Claims, 4 Drawing Sheets

(56) References Cited

FOREIGN PATENT DOCUMENTS

| JP | 2003-180688 A | 7/2003 |
|---|---|---|
| JP | 2004-283265 A | 10/2004 |
| JP | 2005-253699 A | 9/2005 |
| JP | 2005-348758 A | 12/2005 |
| JP | 2006-505319 A | 2/2006 |
| JP | 2008-043531 A | 2/2008 |

OTHER PUBLICATIONS

Japanese Office Action dated Jan. 4, 2011, issued in corresponding Japanese Patent Application No. 2008-310023.
Chinese Office Action dated Aug. 2, 2012 issued in corresponding Chinese Patent Application No. 200910211944.2.
European Office Action dated Apr. 26, 2012, issued in corresponding European Patent Application No. 09014375.1 (5 pages).

\* cited by examiner

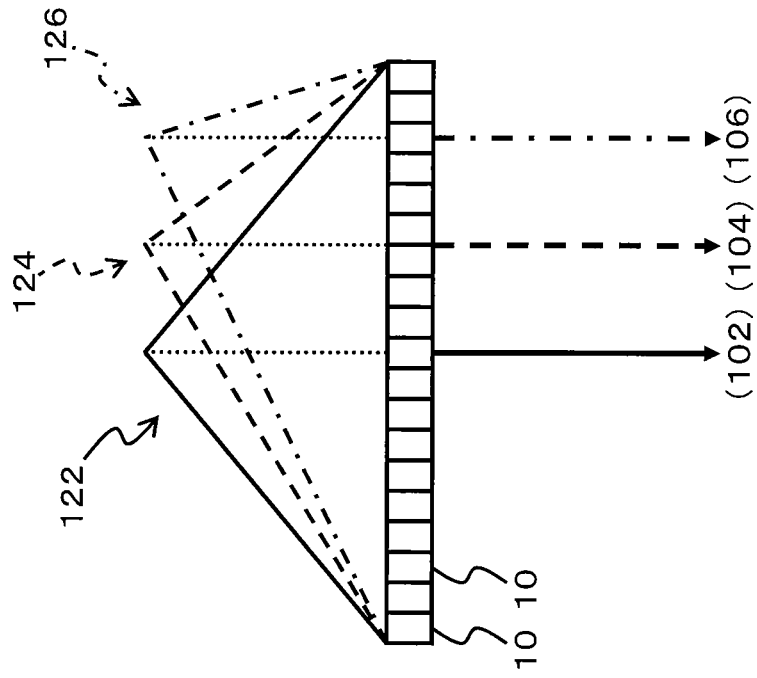
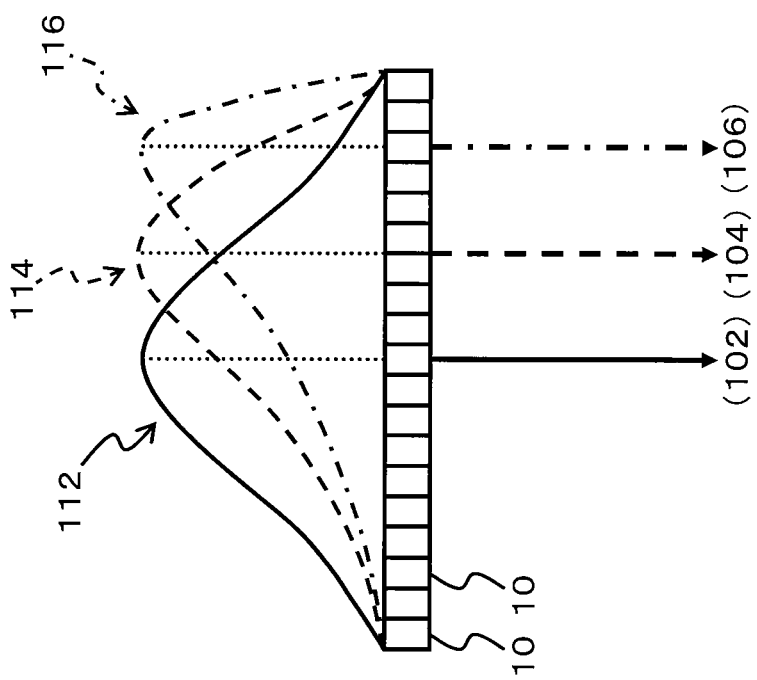

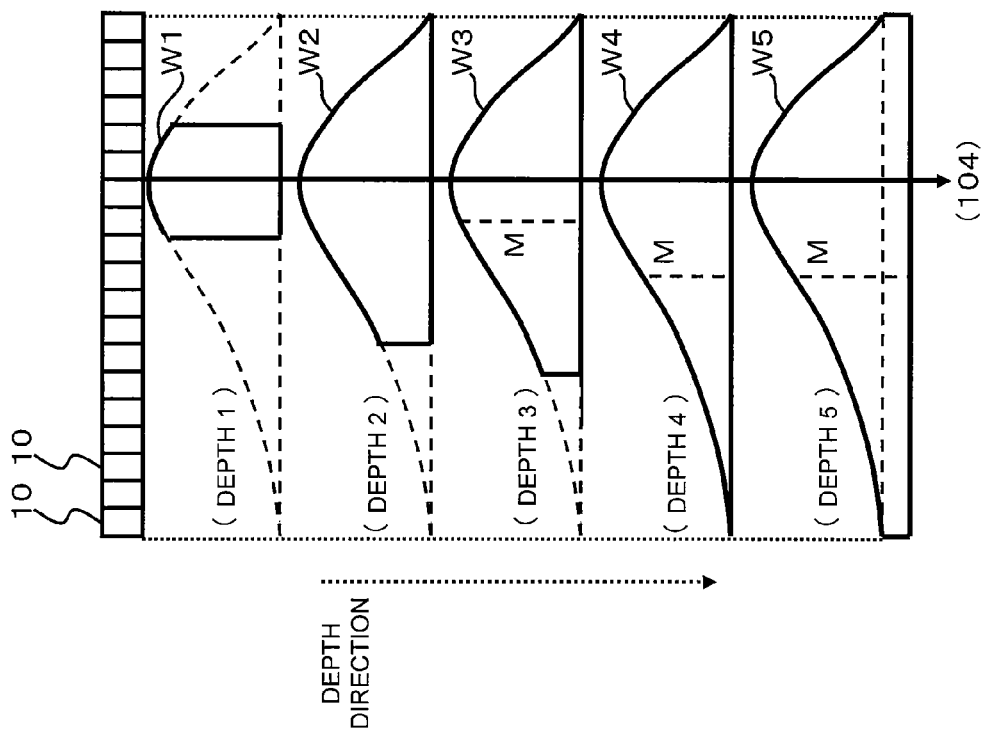
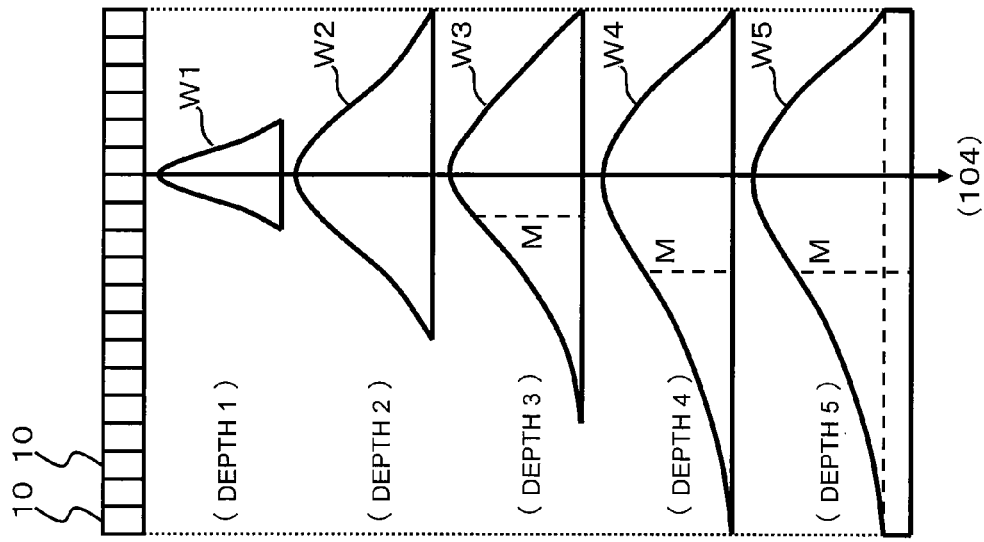
FIG. 4 (A)
FIG. 4 (B)

ULTRASOUND DIAGNOSIS APPARATUS

BACKGROUND

Technical Field

The present invention relates to an ultrasound diagnosis apparatus, and in particular to processing of a received signal.

Related Art

An array-type ultrasound transducer (array transducer) having an array of transducer elements comprising a plurality of transducer elements is known. In addition, in order to reduce side lobes of ultrasound beam during transmission and reception of the ultrasound using the array transducer, a technique is known in which weights are assigned according to positions of the transducer elements in a transmit aperture or a receive aperture.

For example, JP Hei 7-116163 A (Patent Document 1) discloses a technique of reception weighting in which the distribution of the weights is set symmetrical. In Patent Document 1, a position of a peak of the reception weights and the position of the center of the receive aperture are matched regardless of the position of the ultrasound beam (refer to FIG. 9 of Patent Document 1).

JP 2005-253699A (Patent Document 2) and JP 2008-43531A (Patent Document 3) disclose weighting techniques in which the distribution of the weights is not symmetrical. For example, Patent Document 2 discloses that, when the ultrasound beam direction is steered in a slanted direction, a gain difference is caused in signals in the transducer elements according to the change of the path of the ultrasound, and that, in order to correct this gain difference, weights which are not symmetrical (asymmetrical weights) are used. Patent Document 3 discloses a technique to inhibit temperature increase in the probe by alternately switching between asymmetrical weights.

When the distribution of the weights is set symmetrical and the position of the peak of the reception weights and the position of the center of the receive aperture are matched regardless of the position of the ultrasound beam, if the position of the peak of the reception weights is significantly deviated from the position of the ultrasound beam, problems may be caused such as reduction of sensitivity and increase in grating lobe. Such problems cannot be solved by simply setting the distribution of the weights to be asymmetrical.

Under the above-described circumstances, the present inventors have researched and developed weights for the array transducer.

SUMMARY

The present invention was conceived in view of the above-described circumstances, and an advantage of the present invention is that an improved technique is provided for weighting of signals received by the array transducer.

In order to achieve at least the advantage described above, according to one aspect of the present invention, there is provided an ultrasound diagnosis apparatus comprising an array transducer having a plurality of transducer elements, a transmitting unit which outputs a transmission signal to the plurality of transducer elements, and a receiving unit which applies a reception weight on a reception signal obtained from the plurality of transducer elements in a receive aperture, based on a position of each transducer element in the receive aperture, wherein the receiving unit shifts a position of a peak of the reception weights in the receive aperture, to follow a movement of the reception beam.

With the structure of the above-described aspect of the present invention, because the position of the peak of the reception weights is shifted in the receive aperture to follow the movement of the reception beam, advantages such as improvement of the reception sensitivity and reduction of the grating lobe can be obtained compared to a case, for example, in which the position of the peak of the reception weights is fixed at the center of the receive aperture.

According to various aspects of the present invention, an improved technique for reception weights of the array transducer is provided. For example, according to preferred configurations of the present invention, because the position of the peak of the reception weights is shifted in the receive aperture to follow the movement of the reception beam, advantages such as improvement of the reception sensitivity and reduction of the grating lobe can be obtained compared to a case, for example, in which the position of the peak of the reception weights is fixed at the center of the receive aperture.

BRIEF DESCRIPTION OF THE DRAWINGS

An exemplary embodiment of the present invention will be described in detail based on the following figures, wherein:

FIG. 2 is a diagram for explaining a weighting process in a preferred embodiment of the present invention;

FIG. 4 is a diagram for explaining control of the receive aperture according to a depth.

DETAILED DESCRIPTION

A preferred embodiment of the present invention will now be described.

Figure 1:
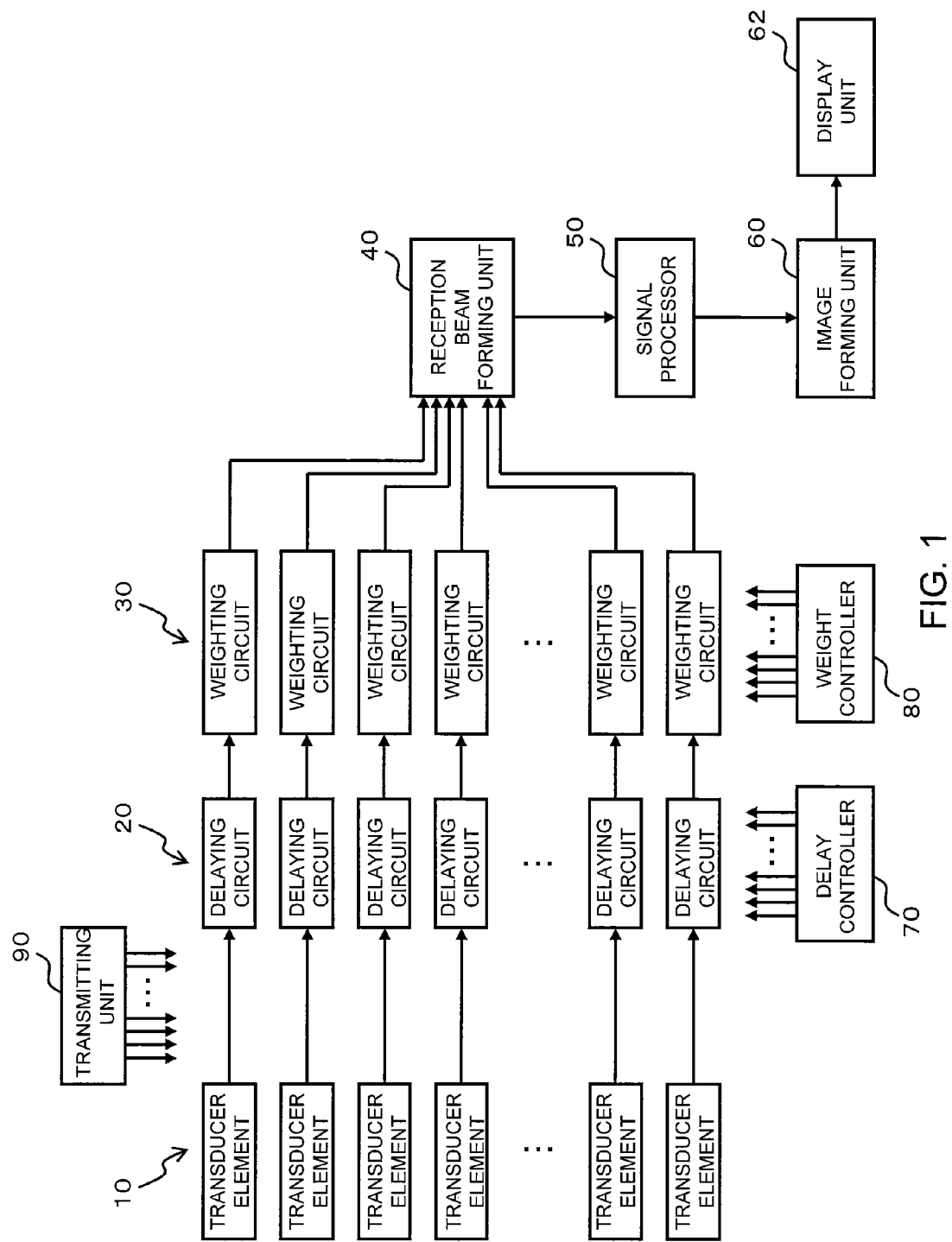
FIG. 1 is a functional block diagram showing an overall structure of an ultrasound diagnosis apparatus according to a preferred embodiment of the present invention.

FIG. 1 shows an ultrasound diagnosis apparatus according to a preferred embodiment of the present invention, and is a functional block diagram showing an overall structure of the ultrasound diagnosis apparatus.

An ultrasound diagnosis apparatus shown in FIG. 1 comprises an array transducer having a plurality of transducer elements 10. The plurality of transducer elements 10 are arranged in a one-dimensional manner. In the present embodiment, for example, a linear-type probe or a convex-type probe is formed by the plurality of the transducer elements 10.

The plurality of transducer elements 10 vibrate according to a transmission signal which is output from a transmitting unit 90, and transmit an ultrasound to, for example, a living body. The transmitting unit 90 supplies a transmission signal to each of the plurality of transducer elements 10. In this process, a delay process or the like is applied to the transmission signal according to the transducer elements 10, to form an ultrasound transmission beam. The transmission beam formation is thus realized, and the ultrasound transmission beam is electrically scanned. The transducer element 10 outputs a reception signal obtained as a result of transmitting the ultrasound.

A delay circuit 20 and a weighting circuit 30 are correlated to each of the plurality of transducer elements 10. The delay circuit 20 is a circuit which applies a delaying process to the reception signal obtained from the corresponding transducer element 10. The plurality of delay circuits 20 are controlled by a delay controller 70. With the delay circuit 20, the delaying process for forming the ultrasound reception beam is applied to the reception signal obtained from the corresponding transducer element 10.

The weighting circuit 30 is a circuit which applies a weighting process according to the corresponding transducer element 10. That is, the weighting circuit 30 applies a weighting process of a voltage (amplitude) on the reception signal for which the delaying process is applied in the corresponding delay circuit 20. The weighting process is executed based on control by a weight controller 80. In the present embodiment, the weighting process is executed to obtain advantages such as, for example, improvement of reception sensitivity and reduction of grating lobe. The weighting process in the present embodiment will be described later in more detail.

A reception beam forming unit 40 forms an ultrasound reception beam based on a reception signal which is output from the plurality of weighting circuits 30. The reception beam forming unit 40 applies, for example, an adding process on the plurality of reception signals to which the delaying process and the weighting process are applied, to realize reception beam formation. A reception beam corresponding to the transmission beam is thus formed and the ultrasound beam (the transmission beam and the reception beam) is electrically scanned.

A signal processor 50 applies a signal process such as detection and logarithmic compression on the reception signal after the phase adding process is applied. Alternatively, an extraction process of Doppler information or the like may be executed in the signal processor 50. The signal processed by the signal processor 50 is supplied to an image forming unit 60. The image forming unit 60 applies a coordinate conversion or an interpolation process on the input signal, and forms a B-mode image or the like. Alternatively, a Doppler waveform or a color Doppler image may be formed based on the Doppler information. An image formed in the image forming unit 60 in this manner is displayed on a display unit 62.

The overall structure of the present embodiment has been described. Next, a weighting process in the present embodiment will be described in detail. In the following description, for portions (structures) shown in FIG. 1, the reference numerals of FIG. 1 will be used.

In the present embodiment, a reception weight is applied to the reception signal obtained from the plurality of transducer elements 10 in the receive aperture, according to the position of the transducer element 10 in the receive aperture. In addition, a position of a peak of the reception weights is shifted in the receive aperture to follow the movement of the reception beam. It is preferable that the magnitude of the reception weight be gradually decreased from the position of the peak of the reception weights toward the ends of the receive aperture.

FIG. 2 is a diagram for explaining the weighting process in the present embodiment. FIG. 2(A) is a conceptual diagram showing an array transducer having the plurality of transducer elements 10, weighting functions 112, 114, and 116 indicating the magnitudes of the receptions weights for the transducer elements 10, and reception beams 102, 104, and 106 which are electrically scanned and are moved. The weighting functions 112, 114, 1nad 116 shown in FIG. 2(A) are Beta density functions. The Beta density function y(x) is represented as follows:

[Equation 1]

Beta density function $y(x):y(x)=x^b(1-x)^c/a$ (1)

$a=b^b \cdot c^c/(b+c)^{b+c}$ (2)

In Equation 1, x represents a coordinate in the array (aperture) direction. That is, x represents a position, within the array, of the transducer element 10 arranged in the one-dimensional manner. In Equation 1, x is normalized within a range of 0~1. In other words, a position of one end of the transducer elements 10 which are arranged in the one-dimensional manner corresponds to a value of 0 and the position of the other end corresponds to a value of 1. In Equation 1, variable a represents a normalization coefficient for setting the maximum value of y(x) to 1, and variables b and c are parameters for controlling degree of skewness of y(x), direction of skew, and area of y(x).

In FIG. 2(A), the reception beams 102, 104, and 106 are formed using all of the transducer elements 10 of the array transducer. In other words, all range of the array transducers is set as receive aperture. All of the transducer elements 10 are used, and, with the electrical scan control, reception beams 102, 104, and 106 at positions which differ from each other are formed.

The reception beam 102 is formed using the weighting function 112. The position of the peak of the weighting function 112, that is, the position of the transducer element 10 having the maximum weight is at the position of the reception beam 102. Similarly, the reception beam 104 is formed using the weighting function 114, and the position of the peak of the weighting function 114 is at the position of the reception beam 104. Finally, the reception beam 106 is formed using the weighting function 116, and the position of the peak of the weighting function 116 is at the position of the reception beam 106.

As shown in FIG. 2(A), in the present embodiment, the positions of the peaks of the weighing functions 112, 114, and 116 are shifted in the receive aperture to follow the movement of the reception beams 102, 104, and 106 by the electrical scan. As a result, in the present embodiment, the sensitivity is improved and the grating lobe is reduced compared to, for example, a case in which the position of the peak of the reception weights is significantly deviated from the position of the reception beam.

In order to not vary the reception sensitivity according to the position of the reception beam, it is desirable to shift the position of the peak of the reception weights while maintaining a total sum of the reception weights at a constant. For example, the areas of the functions of the weighting functions 112, 114, and 116 are desirably equal to each other.

Alternatively, for the reception weighting function, a triangular function as shown in FIG. 2(B) may be used. FIG. 2(B) shows a conceptual diagram of an array transducer having the plurality of transducer elements 10, weighting functions 122, 124, and 126 indicating the magnitudes of the reception weights for the transducer elements 10, and reception beams 102, 104, and 106 which are electrically scanned and are moved.

The weighting functions 122, 124, and 126 shown in FIG. 2(B) are triangular functions, and the reception beam 102 is formed using the weighting function 122. The position of the peak of the weighting function 122, that is, the position of the transducer element 10 having the maximum weight is at the position of the reception beam 102. Similarly, the reception beam 104 is formed using the weighting function 124, and the position of the peak of the weighting function 124 is at the position of the reception beam 104. Finally, the reception beam 106 is formed using the weighting function 126, and the position of the peak of the weighting function 126 is at the position of the reception beam 106.

As shown in FIG. 2, as the position of the reception beam comes closer to the end of the receive aperture, the skewness of the weighting function gradually increases. When the skewness of the weighting function is significantly large, the reduction advantage of the side lobe is weakened. Therefore, in the present embodiment, a restriction area is provided at the end of the array transducer, and the position of the peak of the reception weights is fixed within the restriction area, to inhibit the skewness of the weighting function to become significantly great.

Figure 3:
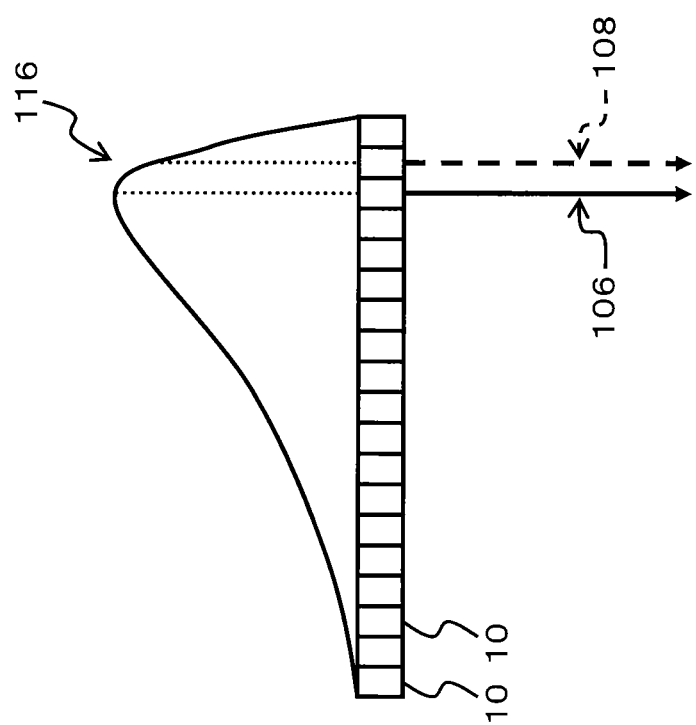
FIG. 3 is a diagram for explaining a reception weighting process in a restriction area.

FIG. 3 is a diagram for explaining the reception weighting process in the restriction area. FIG. 3 shows a conceptual diagram of an array transducer having the plurality of transducer elements 10, a weighting function 116 indicating the magnitudes of the reception weights for the transducer elements 10, and the reception beams 106 and 108 which are electrically scanned and are moved.

The restriction area is provided at an end of the array transducer. For example, in a normalized coordinate in which the position of one end of the array transducer having the plurality of transducer elements 10 arranged in the one-dimensional manner is set as 0 and the position of the other end is set as 1, the area of 0~0.2 on one end and the area of 0.8~1.0 on the other end are set as the restriction area. The area other than the restriction area, for example, the area of 0.2~0.8 of the normalized coordinate is set as a following area.

In FIG. 3, the reception beam 106 is formed at a boundary position between the following area and the restriction area. In other words, the reception beam 106 is formed at the position of 0.8 in the normalized coordinate. In the following area of the normalized coordinate of 0.2~0.8, the position of the peak of the reception weights is shifted in the receive aperture to follow the movement of the reception beam (refer to FIG. 2). Because of this, the position of the peak of the weighting function 116 corresponding to the reception beam 106 matches the position of the reception beam 106.

In the restriction area, on the other hand, the position of the peak of the reception weights is fixed regardless of the movement of the reception beam. For example, in the restriction area of the normalized coordinate of 0.8~1, the weighting function 116 having the position of the peak fixed is used, and the reception beam 108 is formed using the weighting function 116. In the restriction area of normalized coordinate of 0~0.2, the weighting function at the position of 0.2 is used.

As described above, in the present embodiment, the position of the peak of the reception weights is shifted in the following area. In addition, the size of the receive aperture may be changed according to the depth along a depth direction of the reception beam.

FIG. 4 is a diagram for explaining the control of the receive aperture according to the depth. FIG. 4(A) shows an array transducer having the plurality of transducer elements 10 and reception beam 104 formed by the array transducer. In addition, FIG. 4(A) shows a conceptual diagram of the reception weights corresponding to the depths. For example, a weighting function W1 is used in depth 1, and a weighting function W2 is used in depth 2.

The weighting functions W1~W5 in the depth 1 through depth 5 in FIG. 4(A) are formed on the basis of the weighting function W4 at the depth 4. The weighting function W4 at the depth 4 has, for example, the same shape as the weighting function 114 shown in FIG. 2(A).

At the depth 1 which is the shallowest position in FIG. 4(A), the receive aperture is narrowed to a region near the reception beam 104. The function portion corresponding to the aperture portion at the depth 1 is cut out from the weighting function W4, to form the weighting function W1.

At the depth 2, which is deeper than the depth 1, the receive aperture is widened compared to the case of the depth 1. The function portion corresponding to the aperture portion at the depth 2 is cut out from the weighting function W4, to form the weighting function W2. At the depth 3, which is deeper than both the depth 1 and the depth 2, the function portion corresponding to the aperture portion at the depth 3 is cut out from the weighting function W4, to form the weighting function W3.

At the depth 4, which is still deeper than the depth 3, the receive aperture is widened to the entire region of the array transducer, and the weighting function W4 corresponding to the entire region of the array transducer is used. At the depth 5, which is deeper than the depth 4, the weighting function W4 is uniformly raised over the entire region of the array transducer, to form the weighting function W5. At depths deeper than the depth 5, the weighting function W5 may be used or a function may be used in which the weighting function W5 is raised according to the depth.

In FIG. 4(A), the size of the receive aperture is changed according to the depth, from the depth 1 to the depth 4. By narrowing the receive aperture to a region near the reception beam 104 at relatively shallow positions such as the depth 1 through the depth 3, it is possible to reduce the grating lobe. In FIG. 4(A) also, the positions of the peaks of the weighting functions W1~W5 match the position of the reception beam 104 at each depth. At depths from the depth 3 to the depth 5, the center position M of the receive aperture and the position of the reception beam 104 deviate from each other In changing the receive aperture according to the depth, it is possible to change the width of the weighting function according to the size of the receive aperture, as shown in FIG. 4(B). FIG. 4(B) shows a conceptual diagram of the reception weights depending on the depths. For example, the weighting function W1 is used at the depth 1, and the weighting function W2 is used at the depth 2.

In the weighting functions W1~W5 at depths 1 through depth 5 in FIG. 4(B), the width of the function is changed according to the size of the receive aperture. The weighting function W4 at the depth 4 has the same shape as the weighting function 114 shown in FIG. 2(A), for example.

In FIG. 4(B), the receive aperture is narrowed to only a region near the reception beam 104 at the depth 1. The weighting function W1 having a width corresponding to the aperture portion at the depth 1 is formed. As the depth is increased from the depth 1 to the depth 4, the receive aperture is gradually widened, and the width of the function is gradually widened correspondingly, for weighting functions W1~W4.

At the depth 5, the weighting function W4 is uniformly raised over the entire region of the array transducer, to form the weighting function W5. At depths deeper than the depth 5, the weighting function W5 may be used or a function in which the weighting function W5 is raised according to the depth may be used. In FIG. 4(B), at the depth 1 and the depth 2, weighting functions W1 and W2 symmetric to the left and right are used, and, at the depths 3 through depth 5, the center position M of the receive aperture and the position of the reception beam 104 deviate from each other.

The above-described control of the size of the receive aperture according to the depth may also be applied to, for example, a reception dynamic focus control.

A preferred embodiment of the present invention has been described. The above-described preferred embodiment, however, is merely exemplary, and does not limit the scope of the present invention.

What is claimed is:

1. An ultrasound diagnosis apparatus comprising:
an array transducer having a plurality of transducer elements comprising first and second subsets of transducer elements;
a transmitter which outputs a transmission signal to the plurality of transducer elements; and
an weighting circuit and a weight controller for controlling the weighting circuit which are configured to apply a reception weight on a reception signal obtained from the plurality of transducer elements in a receive aperture, based on a position of each transducer element in the receive aperture, wherein
the weighting circuit and the weight controller are configured to shift a position of a peak of the reception weights in the receive aperture, to follow a movement of a reception beam along a direction of scanning in the receive aperture having a reception weight other than zero,
the array transducer comprises a first area composed of the first subset of transducer elements at an end of the array transducer or at ends of the array transducer and a second area composed of the second subset of transducer elements, and
the weighting circuit and the weight controller are configured to allow the position of the peak of the reception weights to follow the movement of the reception beam in a manner that differs between the first area and the second area.

2. The ultrasound diagnosis apparatus according to claim 1, wherein
the weighting circuit and the weight controller are configured to allow the position of the peak of the reception weights to match a position of the reception beam in the second area.

3. The ultrasound diagnosis apparatus according to claim 1, wherein
the weighting circuit and the weight controller are configured to fix the position of the peak of the reception weights in the first area.

4. The ultrasound diagnosis apparatus according to claim 1, wherein
the weighting circuit and the weight controller are configured to change a size of the receive aperture according to a depth along a depth direction of the reception beam.

5. The ultrasound diagnosis apparatus according to claim 1, wherein the weighting circuit and the weight controller are configured to allow the position of the peak of the reception weights to match a position of the reception beam in the second area and to fix the position of the peak of the reception weights in the first area.

6. The ultrasound diagnosis apparatus according to claim 5, wherein
the weighting circuit and the weight controller are configured to change a size of the receive aperture according to a depth along a depth direction of the reception beam.

7. The ultrasound diagnosis apparatus according to claim 5, wherein
the weighting circuit and the weight controller are configured to shift the position of the peak of the reception weights while maintaining a constant value for a total sum of the reception weights in the receive aperture.

8. The ultrasound diagnosis apparatus according to claim 7, wherein
the weighting circuit and the weight controller are configured to change a size of the receive aperture according to a depth along a depth direction of the reception beam.

9. The ultrasound diagnosis apparatus according to claim 7, wherein
the weighting circuit and the weight controller are configured to apply the reception weight based on a Beta density function or a triangular function.

10. The ultrasound diagnosis apparatus according to claim 9, wherein
the weighting circuit and the weight controller are configured to change a size of the receive aperture according to a depth along a depth direction of the reception beam.

11. The ultrasound diagnosis apparatus according to claim 1, wherein
the weighting circuit and the weight controller are configured to shift the position of the peak of the reception weights while maintaining a constant value for a total sum of the reception weights in the receive aperture.

12. The ultrasound diagnosis apparatus according to claim 11, wherein
the weighting circuit and the weight controller are configured to change a size of the receive aperture according to a depth along a depth direction of the reception beam.

13. The ultrasound diagnosis apparatus according to claim 11, wherein
the weighting circuit and the weight controller are configured to apply the reception weight based on a Beta density function or a triangular function.

14. The ultrasound diagnosis apparatus according to claim 13, wherein
the weighting circuit and the weight controller are configured to change a size of the receive aperture according to a depth along a depth direction of the reception beam.

* * * * *